United States Patent
Nishimori et al.

(12)

(10) Patent No.: US 6,340,677 B1
(45) Date of Patent: Jan. 22, 2002

(54) METHOD OF EVALUATION OF SKIN CONDITIONING-AMELIORATING AGENTS AND METHOD OF PRODUCING COMPOSITIONS FOR TOPICAL APPLICATION TO SKIN

(75) Inventors: Yasutomo Nishimori; Katsuo Matsumoto; Yukiko Kenjo, all of Yokohama (JP)

(73) Assignee: Pola Chemical Industries, Inc., Shizuoka (JP)

( * ) Notice: Subject to any disclaimer, the term of this patent is extended or adjusted under 35 U.S.C. 154(b) by 0 days.

(21) Appl. No.: 09/381,149
(22) PCT Filed: Mar. 4, 1998
(86) PCT No.: PCT/JP98/00896
　§ 371 Date: Sep. 13, 1999
　§ 102(e) Date: Sep. 13, 1999
(87) PCT Pub. No.: WO98/40045
　PCT Pub. Date: Sep. 17, 1998

(30) Foreign Application Priority Data

Mar. 11, 1997 (JP) .............................................. 9-074353

(51) Int. Cl.⁷ .............................................. A61K 31/56
(52) U.S. Cl. ........................ 514/169; 514/171; 514/557; 514/574
(58) Field of Search ................................ 514/169, 171, 514/557, 574

(56) References Cited

U.S. PATENT DOCUMENTS 4,835,102 A　5/1989　Bell et al.
5,547,988 A　8/1996　Yu et al.

FOREIGN PATENT DOCUMENTS

EP　0 379 367 A2　7/1990
JP　4-124118　4/1992
JP　5-139947　6/1993
JP　6-48934　2/1994
JP　6-247837　9/1994
JP　7-33651　2/1995
JP　7-187985　7/1995
JP　8-231368　9/1996

OTHER PUBLICATIONS

Bernard Coulomb, Ph.D., et al., Influence of Human Dermal Fibroblasts on Epidermalization, The Journal of Investigative Dermatology, vol. 92, No. 1, Jan. 1989, pp. 122–125.
Raphael Warren, Ph.D., et al., Age, sunlight, and facial skin: A histologic and quantitative study, Journal f the American Academy of Dermatology, vol. 25, No. 5, Part 1, Nov. 1991.
Yoshimitsu Kuroyanagi, et al., Cytotoxicity tests for antimicrobial agents using cultured skin substitutes fixed at interface of air and culture medium, J. Biomater. Sci. Polymer Edn. vol. 7 No. 11 pp. 1005–1015 (1996).
A consumer's Dictionary of Cosmetic Ingredients, Ruth Winter, M.S., New, Third Revised Edition, Crown Publisher, Inc., New York, pp. 84, COLETH–24.

*Primary Examiner*—Zohreh Fay
(74) *Attorney, Agent, or Firm*—Knobbe, Martens, Olson & Bear, LLP

(57) ABSTRACT

An object of the present invention is to provide a means of appropriately evaluating a skin conditioning-ameliorating agent for ameliorating bad skin conditions or preventing the skin conditions from getting worse and a composition for topical application to skin containing the above agent. The invention provides a method for evaluating a skin conditioning-ameliorating agent or a composition for topical application to skin containing the same using an animal having at least one skin portion with bad conditions, which comprises applying to the skin portion the skin conditioning-ameliorating agent or the composition for topical application to skin containing the agent and evaluating the agent or the composition using as an index changes of the degree of order of dermis collagen fiber bundle at the skin portion before and after application.

12 Claims, 7 Drawing Sheets

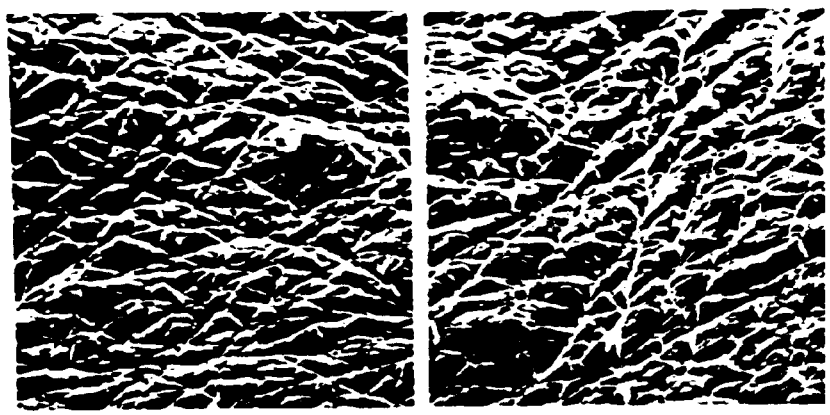
A          B
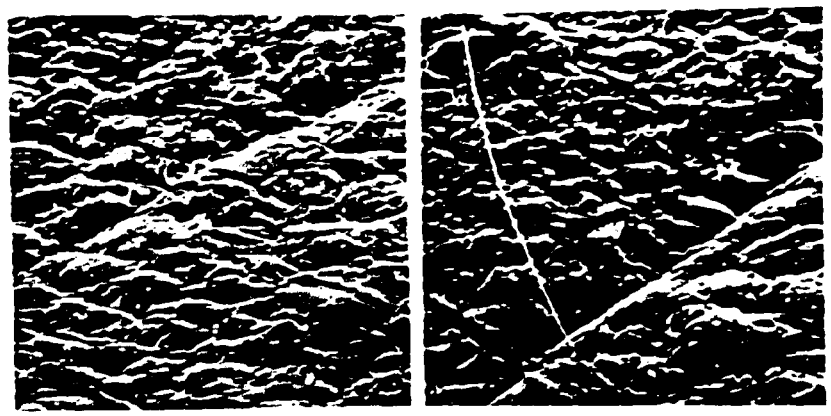
C          D
F I G. 1

E  F

G  H

 
M  N
 
O  P
F I G. 4

Q R

S T

U  V

W  X

METHOD OF EVALUATION OF SKIN CONDITIONING-AMELIORATING AGENTS AND METHOD OF PRODUCING COMPOSITIONS FOR TOPICAL APPLICATION TO SKIN

This application is the U.S. National Phase under 35 U.S.C. §371 of International Application PCT/JP98/00896, filed Mar. 4, 1998, which claims priority based on JP 9-074353, filed Mar. 11, 1997.

FIELD OF THE INVENTION

The present invention relates to a method for appropriate evaluation of skin conditioning-ameliorating agents for improving unfavorable skin conditions such as wrinkles or chapped skin or preventing skin conditions from getting worse and compositions for topical application to skin for use in ameliorating skin conditions (hereinafter sometimes simply referred to as "composition for topical application to skin") containing the above agents and to a method of producing compositions for topical application to skin having a sufficient skin conditioning-ameliorating effect.

BACKGROUND OF THE INVENTION

Though everybody cannot stop seeking beautiful and clear skins, skin conditions change due to various factors. For example, formation of wrinkles varies depending on age, taking care of the skin or damages caused by light or the like. At present, there is no. established theory for such basic questions as "what wrinkles are" or "why wrinkles form". Further, there are various theories such that "wrinkles are caused by the change of the structure of elastin" or that "wrinkles are attributed to decrease of the amount of collagen". However, phenomenon contrary to these theories are sometimes observed. Thus, changes of skin conditions represented by formation of wrinkles have not been elucidated completely without contradiction.

On the other hand, a number of skin conditioning-ameliorating agents and compositions for topical application to skin containing such agents have been developed so far to ameliorate unfavorable skin conditions such as wrinkles as described above or to prevent worsening of such skin conditions. Evaluation of such agents had to largely depend on the method of functionally evaluating changes of the skin surface on which the above skin conditioning-ameliorating agent is applied. In other words, there was no universal evaluation standard to screen, from various drugs and preparations, those enabling amelioration of the skin conditions or prevention of their worsening as described above, and therefore, appropriate evaluation could not be given to skin conditioning-ameliorating agents and compositions for topical application to skin containing such agents.

Thus, in order to seek methods for ameliorating skin conditions or preventing skin conditions from getting worse, it is very important to identify changes of skin conditions correctly, particularly quantitatively. Nevertheless, such identification methods have not been obtained so far. Thus, it has been desired to develop methods for identifying changes of skin conditions correctly for appropriate evaluation of skin conditioning-ameliorating agents and the like.

SUMMARY OF THE INVENTION

Under these circumstances, the present invention was made. An object of the present invention is to provide a method for appropriately evaluating a skin conditioning-ameliorating agent for improving unfavorable skin conditions or preventing skin conditions from getting worse and a composition for topical application to skin containing the above agent for use in ameliorating skin conditions. Another object of the present invention is to provide a method of producing a composition for topical application to skin containing the skin conditioning-ameliorating agent, which has a sufficient skin conditioning-ameliorating effect.

The term "skin conditioning-ameliorating agents" used herein means drugs consisting of only effective components for amelioration of skin conditions having a skin conditioning-ameliorating effect or an effect to prevent worsening of skin conditions.

In order to achieve the above objects, the present inventors sought means of appropriately identifying changes of skin conditions such as wrinkles by conscientiously observing tissues in the course of actual formation of wrinkles. As a result of intensive investigations, it was found that the structure of collagen fiber bundle in dermis was in disorder and is unclear when the skin conditions were unfavorable such as wrinkles or chapped skin. In other words, it was found that skin conditions and their changes such as wrinkle formation or amelioration of wrinkles could be identified by using the degree of order of collagen fiber bundle in dermis as an index, thereby completing the present invention. It has not been known at all so far that skin surface morphology and dermis morphology correlate well to each other, particularly that a groove corresponding to a wrinkle on the skin surface is formed as well as on dermis.

Thus, the present invention provides a method for evaluating a skin conditioning-ameliorating agent or a composition for topical application to skin containing the agents using an animal having at least one skin portion with bad conditions, which comprises the steps of applying to the skin portion the skin conditioning-ameliorating agent or the composition for topical application to skin containing the agent and evaluating the agent or the composition using as index changes of the degree of order of dermis collagen fiber bundle at the skin portion before and after application of the agent or the composition.

According to the evaluation method of the present invention, a skin conditioning-ameliorating agent or a composition for topical application to skin containing the agent that can greatly ameliorate the degree of order of dermis collagen fiber bundle is considered to be excellent in a skin conditioning-ameliorating effect.

Animals for use in the method for evaluation of the present invention have at least one skin portion with bad conditions. Specifically, the bad conditions of skin include wrinkles, chapped skin, and the like.

The animals having at least one skin portion with bad conditions used in the present invention specifically include mice which have been exposed to irradiation of ultraviolet light for a long time, guinea pigs whose skin on the back has been shaven and coated with an anionic surface active agent, and the like.

According to the method for evaluation of the present invention, the degree of order of dermis collagen fiber bundle can be determined by taking microphotographs of a specimen of dermis, which has been prepared by excising at least a part of the above-described skin portion, at magnifications of 100 to 10,000 and judging the microphotographs based on the following criterion.

[Criterion for judging]

0: No collagen fiber bundle structure is observed in all observation area.

1: Disintegration or conversion to abnormal structure of collagen fiber bundle structure is observed in more than half of the observation area.

2: Disintegration or denaturation of collagen fiber bundle structure is observed in part, but almost normal structure is retained as a whole.

3: Normal collagen fiber bundle structure is observed over the whole area with almost no disintegration and denaturation.

When the above criterion for judging is used for the degree of order of collagen fiber bundle of dermis in the evaluation method of the present invention, skin conditioning-ameliorating agents and the like that are given better scores after their application than those before their application are considered to be excellent in a skin conditioning-ameliorating effect.

The present invention also relates to a method of producing a composition for topical application to skin containing a skin conditioning-ameliorating agent and provides a method of producing a composition for topical application to skin which comprises the steps of providing an animal having at least one skin portion with bad conditions, applying to the skin portion the composition for topical application to skin once per day for consecutive 8 weeks in an amount of 0.01 g/10 cm$^2$/one application, taking microphotographs of a specimen of dermis prepared by excising at least a part of the skin portion, at magnifications of 100 to 10,000, judging the microphotographs based on the above-described criterion for judging to determine the degree of order of dermis collagen fiber bundle of the part of the skin portion before and after application of the composition, and adjusting the content of the skin conditioning-ameliorating agent so that the value calculated by dividing the degree of order of dermis collagen fiber bundle after application of the composition by that before application should be not less than 1.5.

Specifically, the composition for topical application to skin to which the above method of the present invention can be applied includes wrinkle-ameliorating cosmetics, chapped skin-ameliorating cosmetics, and the like.

BRIEF DESCRIPTION OF THE DRAWINGS

FIG. 1 is electron microphotographs (50 magnification) showing morphological changes of the skin surface of the mouse photo-aging model. A is a photograph taken before ultraviolet light irradiation, B is a photograph taken 2 weeks after initiation of the irradiation, C is a photograph taken 5 weeks after initiation of the irradiation, and D is a photograph taken 10 weeks after initiation of the irradiation.

FIG. 4 is electron microphotographs (2,500 magnification) showing changes of the dermis collagen fiber bundle structure of the mouse photo-aging model. M is a photograph taken before ultraviolet light irradiation, N is a photograph taken 2 weeks after initiation of the irradiation, 0 is a photograph taken 5 weeks after initiation of the irradiation, and P is a photograph taken 10 weeks after initiation of the irradiation.

DETAILED DESCRIPTION OF THE INVENTION

Figure 2:
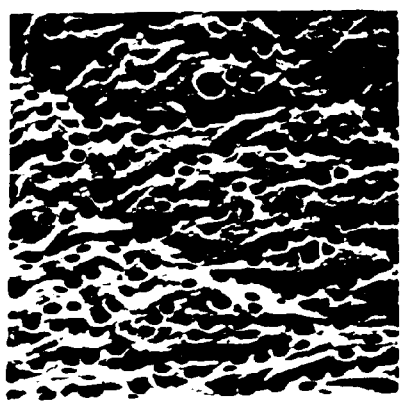
FIG. 2 is electron microphotographs (50 magnification) showing changes of morphology of the surface of dermis of the mouse photo-aging model. E is a photograph taken before ultraviolet light irradiation, F is a photograph taken 2 weeks after initiation of the irradiation, G is a photograph taken 5 weeks after initiation of the irradiation, and H is a photograph taken 10 weeks after initiation of the irradiation.
Figure 2:
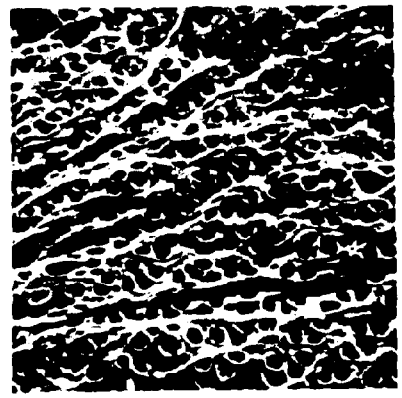
Figure 2:
Figure 2:
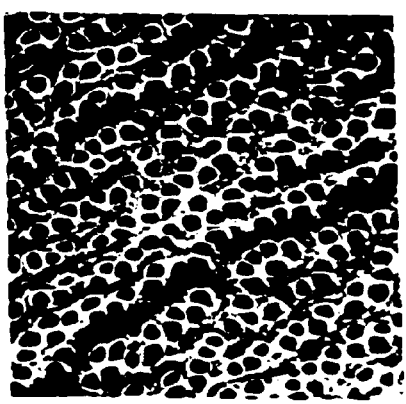

The present invention will be described in detail below.
(1) Evaluation method of the present invention As described above, the present inventors found that skin conditions and their changes can be identified by using the degree of order of collagen fiber bundle in dermis as an index. Utilizing this technique, the evaluation method of the invention comprises preparing or obtaining an animal having at least one skin portion which is in a bad condition in advance, applying a test substance such as a skin conditioning-ameliorating agent to the skin portion, monitoring changes of skin conditions affected by the test substance using changes of the degree of order of collagen fiber bundle in dermis as an index to quantitatively determine the skin conditioning-ameliorating effect of the test substance.

In this occasion, by selecting the skin with bad conditions of the animals having at least one skin portion with such bad conditions so as to meet the object, it is possible to evaluate and screen skin conditioning-ameliorating agents or compositions for topical application to skin, which are suitable for ameliorating the selected bad conditions of skin, for example, wrinkles, chapped skin, or the like.

Examples of the animals having at least one skin portion with such bad conditions include those already established as experimental animals, such as mice exposed to long term irradiation of ultraviolet light (hereinafter sometimes referred to as "mouse photo-aging model"), guinea pigs whose shaven skin is treated with a chemical including an anionic surface active agent such as sodium laurylsulfate (hereinafter sometimes referred to as "guinea pig damaged skin model"), and animal models including animals stimulated with a stimulant to induce inflammation. Alternatively, it is possible to use as panelists human subjects suffering from chapped skin or wrinkles.

However, the use of human subjects must be accompanied with biopsy and the like operations. Thus, it is preferable to use the above-described animal models. Among these animals, the above-described mouse photo-aging model and guinea pig damaged skin model are preferably used as the animals having at least one skin portion with bad conditions used in the present invention. Further, in the evaluation method of the present invention, guinea pigs whose shaven skin on the back is treated with an anion surfactant are preferably used among the guinea pig damaged skin model. According to the present invention, the mouse photo-aging model is suitably used for evaluating and screening the skin conditioning-ameliorating agents or the compositions for topical application to skin, which are appropriate for ameliorating wrinkles and the guinea pig damaged skin model is suitably used for those appropriate for ameliorating chapped skin.

Further, in the evaluation method of the present invention, any method can be non-limitedly used for applying the skin conditioning-ameliorating agents or the compositions for topical application to skin containing the agents on the skin portion with bad conditions of the above animals as long as it enables quantitative application. It is possible to dilute the above skin conditioning-ameliorating agents or the like with an appropriate diluting agent upon application.

Dermis necessary for determining the degree of order of dermis collagen fiber bundle in the evaluation method of the present invention can be obtained by excising a part of skin to be examined and treating this by the usual method. Such a dermis specimen can be obtained from skin by, for example, NaOH method, which comprises treating skin excised as described above with NaOH. Dermis collagen fiber bundle can be seen by observing a dermis specimen obtained as described above under electron microscope. The degree of order of dermis collagen fiber bundle can be determined by, for example, analyzing images of electron microscope or scoring such images under observation by naked eyes based on appropriate criterion for judging.

Specifically, the degree of order of dermis collagen fiber bundle from images of electron microscope under observation by naked eyes can be determined by the method which comprises taking photographs of images of electron microscope of the above-described dermis specimen at about 100 to 10,000 magnification, preferably about 500 to 2,500 magnification, and judging the thus-obtained photographs based on, for example, the following criterion for judging.

[Criterion for judging]

0: No collagen fiber bundle structure is observed in all observation area.

1: Disintegration or conversion to abnormal structure of collagen fiber bundle structure is observed in more than half of the observation area.

2: Disintegration or denaturation of collagen fiber bundle structure is observed in part, but almost normal structure is retained as a whole.

3: Normal collagen fiber bundle structure is observed over the whole area with almost no disintegration and denaturation.

The criterion for judging is not limited to the above, and it is possible to, for example, divide the standard in more detail. However, it is appropriate to use the above criterion basically in the present invention considering the time required for judging and universality of judging, and the like.

In this way, the degree of order of dermis collagen fiber bundle can be determined according to the evaluation method of the present invention. The skin conditioning-ameliorating agents or the like that can greatly ameliorate the degree of order of dermis collagen fiber bundle after its application as compared with that before its application are considered to be excellent in skin conditioning-ameliorating effect. For example, when the above criterion for judging is used in the evaluation method of the present invention, the skin conditioning-ameliorating agents that are given better scores after their application than those before their application are considered to be excellent in skin conditioning-ameliorating effect. In this case, it is possible to calculate a difference or ratio of the scores before and after the application and to use this value for evaluation of the skin conditioning-ameliorating effect.

Since a part of skin is excised to determine the degree of order of dermis collagen fiber bundle according to the evaluation method of the present invention, it is impossible to actually determine the degree of order of dermis collagen fiber bundle in the completely same part of the skin before and after the application of the skin conditioning-ameliorating agent or the like. However, this method requires a trace amount of skin to be excised and it is considered that the substantially same skin portion is determined before and after the application by excising the skin part after the application, which is the closest part to that excised before the application.

When several animals having bad skin conditions in the completely same manner such as the above animal models are used as the animals having at least one skin portion with bad conditions in the evaluation method according to the present invention, the degree of order of dermis collagen fiber bundle of individual animals to which a test compound such as a skin conditioning-ameliorating agent or the like has not been applied is determined to serve as the score before the application, while, separately, the degree of order of dermis collagen fiber bundle of the other animals to which the test compound has been applied is determined to serve as the score after the application, thereby calculating the changes of the degree of order of dermis collagen fiber bundle before and after the application to use the value as an index for evaluation of the test compound.

Further, the evaluation method of the present invention can be applied to evaluation of drugs other than those for subcutaneous application having a skin conditioning-ameliorating effect.

The followings demonstrate an example of evaluation and screening of wrinkle-ameliorating agents when the mouse photo-aging model was used as the wrinkle model and an example of evaluation and screening of chapped skin-ameliorating agents when the guinea pig damaged skin model was used as the chapped skin model.

1) Evaluation of Wrinkle-ameliorating Agents Using the Mouse Photo-aging Model as the Wrinkle Model First, the mouse photo-aging model was prepared to study the relation between changes of skin conditions of the mouse and changes of the degree of order of dermis collagen fiber bundle during the preparation of the model.

a) Relation Between Changes of Skin Conditions and Changes of the Degree of Order of Dermis Collagen Fiber Bundle on the Mouse Photo-aging Model Five groups of hairless mice (Skh: HR-1,female, 8-week-old), each group comprising six mice, were prepared. A part of skin and replica of skin surface morphology were excised from each mouse of one group of them when they were 8 weeks old without the following ultraviolet light irradiation, namely in-the state of before the ultraviolet light irradiation. About the remaining four groups, each mouse was irradiated with ultraviolet light B (Toshiba SE lamp, 60 mJ/cm$^2$) once per day for 5 days a week and fed up.

The irradiation of the ultraviolet light to one group among the four groups described-above was stopped after one week of the initiation of the irradiation and at this time a part of skin and replica of skin surface morphology were excised from each mouse of the group. As the same manner, the irradiation of the ultraviolet light to the another group and to the further another group were stopped after two and five weeks of the initiation of the irradiation and then a part of skin and replica of skin surface morphology were excised from each mouse of the groups respectively. The irradiation of the ultraviolet light to the last group was continued to 10 weeks after initiation of the irradiation to prepare the mouse photo-aging models. Thus the total amount of the ultraviolet light irradiated to the mouse photo-aging models was 3J/cm$^2$. A part of skin and replica of skin surface morphology were also excised from each mouse photo-aging model obtained above.

After taking photographs of scanning electron microscope of the surface morphology of the skin samples excised from mice of the each group as described-above at 50 magnification, dermis specimens were prepared from the above skin samples by NaOH method to-take photographs of scanning electron microscope of the surface morphology at 50 magnification and the collagen fiber bundle structure of the dermis specimens thus obtained at 500 and 2,500 magnifications.

Figure 3:
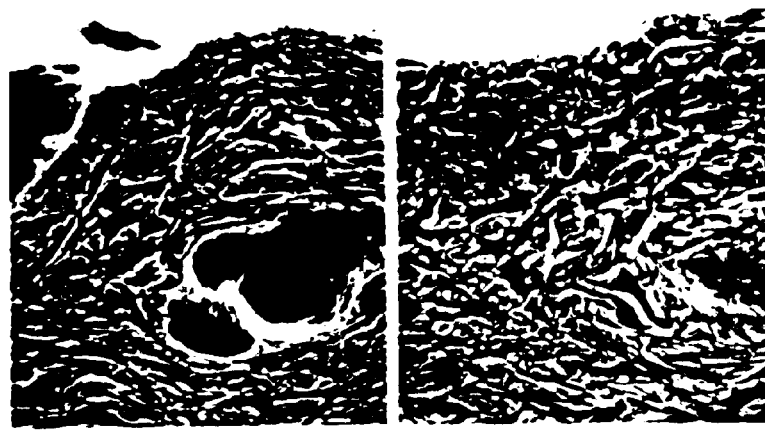
FIG. 3 is electron microphotographs (500 magnification) showing changes of the dermis collagen fiber bundle structure of the mouse photo-aging model. I is a photograph taken before ultraviolet light irradiation, J is a photograph taken 2 weeks after initiation of the irradiation, K is a photograph taken 5 weeks after initiation of the irradiation, and L is a photograph taken 10 weeks after initiation of the irradiation.
Figure 3:
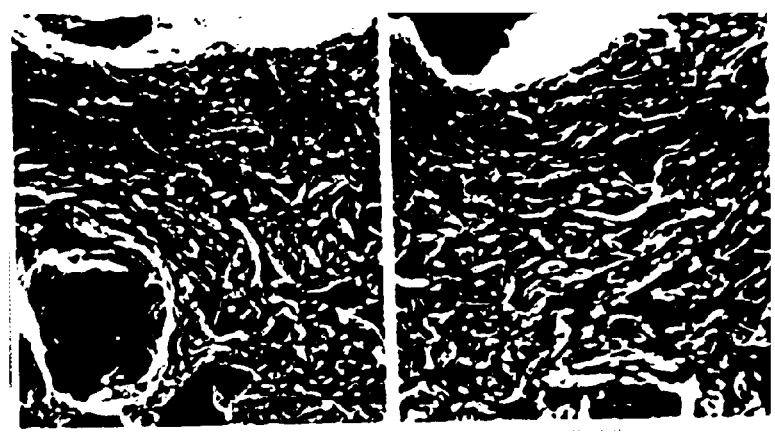

FIG. 1 shows electron microphotographs of the skin surface morphology of a typical individual among six mice of the above-described each group except the group irradiated with ultraviolet light for one week at 50 magnification (A: before the ultraviolet light irradiation, B: 2 weeks after initiation of the irradiation, C: 5 weeks after initiation of the irradiation, and D: 10 weeks after initiation of the irradiation), FIG. 2 shows electron microphotographs of morphology of the dermis surface of the same at 50 magnification (E: before the ultraviolet light irradiation, F: 2 weeks after initiation of the irradiation, G: 5 weeks after initiation of the irradiation, and H: 10 weeks after initiation of the irradiation), FIG. 3 shows electron microphotographs of the dermis collagen fiber bundle structure of the same at 500 magnification (I: before the ultraviolet light irradiation, J: 2 weeks after initiation of the irradiation, K: 5 weeks after initiation of the irradiation, and L: 10 weeks after initiation of the irradiation), FIG. 4 shows electron microphotographs of the dermis collagen fiber bundle structure of the same at 2,500 magnification (M: before the ultraviolet light irradiation, N: 2 weeks after initiation of the irradiation, 0: 5 weeks after initiation of the irradiation, and P: 10 weeks after initiation of the irradiation).

From these figures, it can be seen that, upon formation of wrinkles, grooves are formed on the surface of dermis so as to correspond to the wrinkles and changes of morphology of the skin surface correlate to changes of morphology of the dermis surface. It can also be found that the changes on the dermis surface reflect changes of the structure of dermis collagen fiber bundle, that is, a decrease in order of collagen fiber bundle including becoming unclear of collagen fiber bundle.

Figure 5:
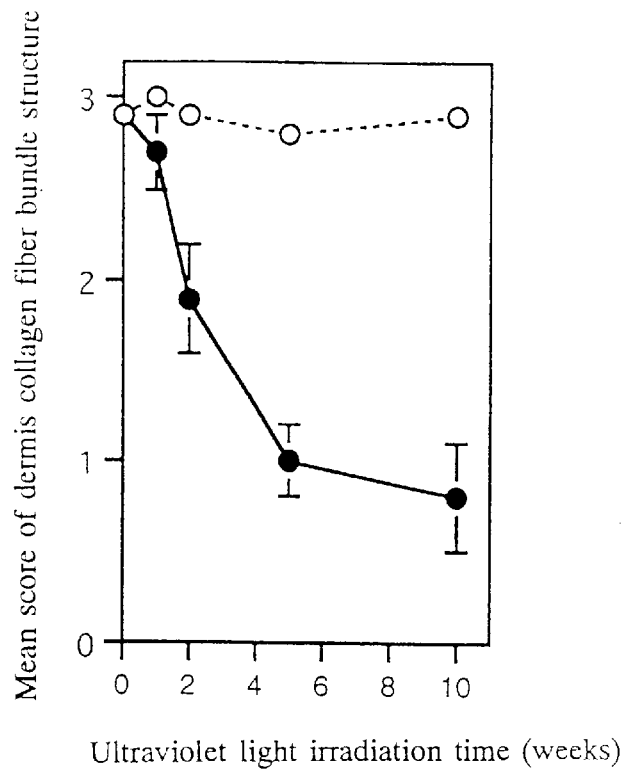
FIG. 5 shows time-course changes of the dermis collagen fiber bundle structure of the mouse photo-aging model in terms of relationship between the evaluated values resulted from judgment of the same photographs as shown in FIG. 4 with a certain standard and the ultraviolet light irradiation time. "●" stands for the plot for the mouse photo-aging model and "○" for the plot for the non-irradiated control mouse.

Based on electron microphotographs of the dermis collagen fiber bundle structure of the above-described mice groups of before the ultraviolet light irradiation, 1 week after initiation of the irradiation, 2 weeks after initiation of the irradiation, 5 weeks after initiation of the irradiation, and 10 weeks after initiation of the irradiation (= mouse photo-aging model) at 2,500 magnification, the dermis collagen fiber bundle structures of mice of the each group were scored 0 to 3 in accordance with the above-described criterion for judging respectively. From the results obtained, an average of the scores in six mice of the each group based on the ultraviolet light irradiation-time and a standard deviation of them were calculated. The average of the scores of the group of 10 weeks after initiation of the irradiation, namely the group of mouse photo-aging models was 0.82. The thus-obtained average values of the groups are shown as "•" plots in FIG. 5 together with the above standard deviation. In FIG. 5, "○" plots stand for the average of the scores for the mouse dermis collagen fiber bundle structure evaluated in the same manner as described above when five groups hairless mice (Skh: HR-1,female, 8-week-old), each group comprising five mice, were separately fed from above-mentioned mice without ultraviolet light irradiation (mice treated in this way are hereinafter referred to as "non-irradiated control mice"). In FIG. 5, the abscissa shows the ultraviolet light irradiation time and the ordinate shows the scores for the mouse dermis collagen fiber bundle structure evaluated in the manner as described above.

Figure 6:
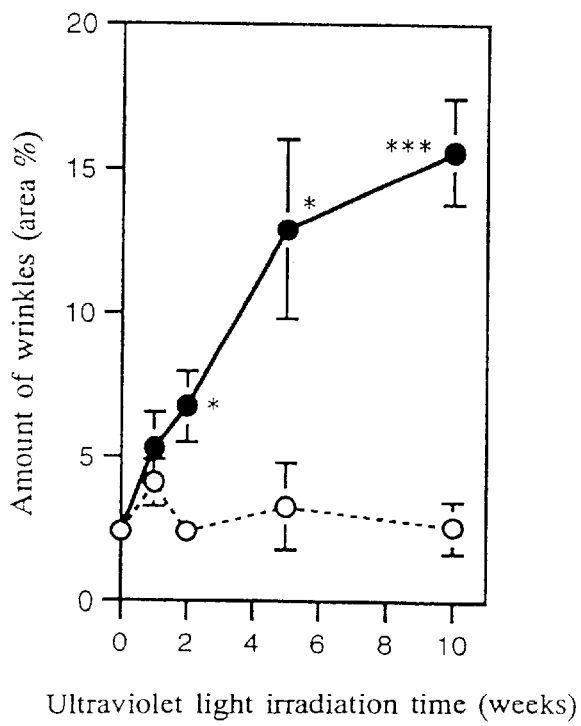
FIG. 6 shows relationship between the amount of wrinkles (area of wrinkles %) of the skin surface determined by analysis of the image and the ultraviolet light irradiation time. "●" stands for the plot for the mouse photo-aging model and "○" for the plot for the non-irradiated control mouse.

Further, the state of structural changes of the mouse skin surface during the preparation of the above mouse photo-aging model was examined in terms of changes of the amount of wrinkles measured by the following method. Namely, the skin surface replica excised from mice of the above-described groups, each group was irradiated with ultraviolet light for different time, were exposed to xenon lamp at an incident angle of 20 and the image of the resulting shadow of-wrinkles was quantitatively analyzed to determine the amount of wrinkles. The amount of wrinkles is shown as percent (%) of the area of wrinkles against the total skin area. The average and standard deviation of the thus-measured amount of wrinkles of six mice of each group were calculated. The resulting average values are shown as "•" plots in FIG. 6 together with the above standard deviation. In FIG. 6, "○" plots stand for the average of the amount of wrinkles measured in the same manner as described above for the non-irradiated control mice. In FIG. 6, the abscissa shows the ultraviolet light irradiation time and the ordinate shows the amount of wrinkles measured in the manner as described above.

From FIG. 5 and FIG. 6, it can be seen that changes of the amount of wrinkles on the skin surface upon preparation of the mouse photo-aging model correlate well with changes of the degree of order of dermis collagen fiber bundle. A correlation coefficient between the average of the amount of wrinkles as obtained above and the average of the scores resulted from evaluation of the degree of order of dermis collagen fiber bundle was calculated as 0.91, which means that the amount of wrinkles can be quantified in terms of the score resulted from evaluation of the degree of order of dermis collagen fiber bundle.

Next, the thus-obtained mouse photo-aging model was used to examine how skins with bad conditions such as wrinkles formed by the ultraviolet light irradiation change by the skin conditioning-ameliorating agents or the compositions for topical application to skin and evaluation of wrinkle-ameliorating agents was carried out in accordance with the evaluation method of the present invention.

b) Evaluation and Screening of Wrinkle-ameliorating Agents A 0.05% solution of dexamethasone in ethanol in the form of a lotion was applied to the mouse photo-aging models (the mice irradiated with ultraviolet light for ten weeks) as obtained by the same manner as described above and then the skin conditions and the degrees of order of dermis collagen fiber bundle of the mice were analyzed in the same manner as described above to evaluate dexamethasone as a wrinkle-ameliorating agent.

Specifically, a 0.05% solution of dexamethasone in ethanol was applied to the test portion of each mouse of five animals per group of the mouse photo-aging model, while only ethanol was applied to the test portion of each mouse of five animals per group as control. Each of the solution was given in an amount of 0.05 ml once a day for consecutive 8 weeks. After completion of the application, a part of the skin was excised from each mouse to take photographs of its surface morphology under scanning electron microscope. Further, dermis specimens were prepared from the skins excised as above in the same manner as described above to take photographs of their surface morphology and the collagen fiber bundle structure under scanning electron microscope.

Figure 7:
FIG. 7 shows electron microphotographs (50 magnification) showing morphological changes of the skin surface in the progress of amelioration of wrinkles in the mouse photo-aging model. Q is a photograph of the ethanol-applied mouse and R shows a photograph of the dexamethasone-applied mouse.
Figure 7:
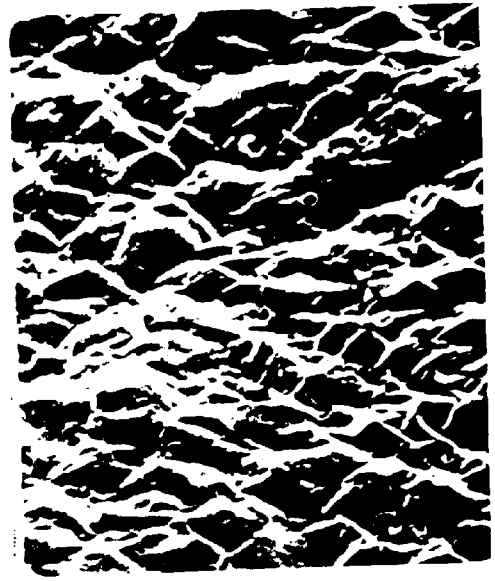
Figure 8:
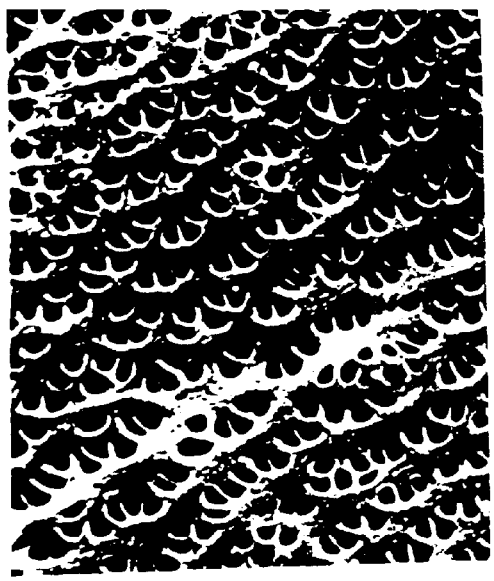
FIG. 8 shows electron microphotographs (50 magnification) showing changes of morphology of the surface of dermis in the progress of amelioration of wrinkles in the mouse photo-aging model. S is a photograph of the ethanol-applied mouse and T shows a photograph of the dexamethasone-applied mouse.
Figure 8:
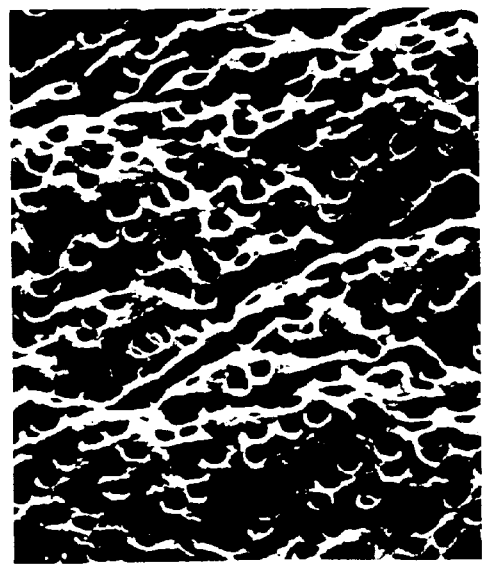
Figure 9:
FIG. 9 shows electron microphotographs (500 magnification) showing changes of the dermis collagen fiber bundle structure in the progress of amelioration of wrinkles in the mouse photo-aging model. U is a photograph of the ethanol-applied mouse and V shows a photograph of the dexamethasone-applied mouse.
Figure 9:
Figure 10:
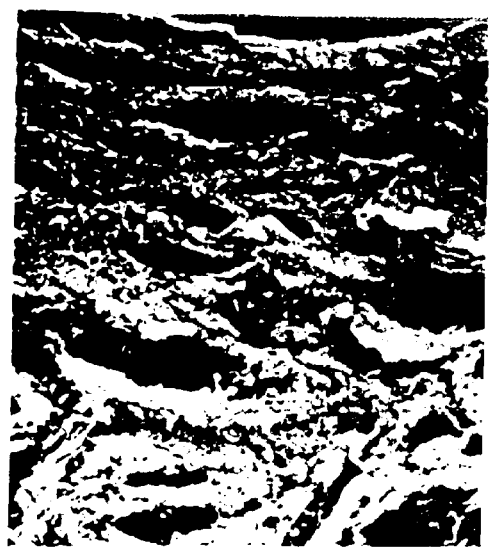
FIG. 10 shows electron microphotographs (2,500 magnification) showing changes of the dermis collagen fiber bundle structure in the progress of amelioration of wrinkles in the mouse photo-aging model. W is a photograph of the ethanol-applied mouse and X shows a photograph of the dexamethasone-applied mouse.
Figure 10:

FIG. 7 shows electron microphotographs of the skin surface morphology of each of typical individuals among five mice per group at 50 magnification (Q: ethanol-applied mouse, R: dexamethasone-applied mouse). FIG. 8 shows electron microphotographs of morphology of the dermis surface at 50 magnification (S: ethanol-applied mouse, T: dexamethasone-applied mouse). FIG. 9 shows electron microphotographs of the dermis collagen fiber bundle structure at 500 magnification (U: ethanol-applied mouse, V: dexamethasone-applied mouse). FIG. 10 shows electron microphotographs of the dermis collagen fiber bundle structure at 2,500 magnification (W: ethanol-applied mouse, X: dexamethasone-applied mouse).

The above-described FIGS. 1 to 4 and these figures indicate that the dexamethasone-applied mice showed excellent amelioration of skin conditions in the skin surface morphology as compared with the ethanol-applied mice. Similar amelioration was observed for the degree of order of collagen fiber bundle of dermis.

Further, based on the microphotographs of the dermis collagen fiber bundle structure taken at 2,500 magnification as obtained above, the degree of order of dermis collagen fiber bundle of the mice in the ethanol-applied group and the mice in the dexamethasone-applied group were scored 0 to 3 in accordance with the above-described criterion for Judging. As a result, an average of the scores in five mice in the ethanol-applied group was 0.78, while an average of the scores in five mice in the dexamethasone-applied group was 1.71.

Comparing these values with the scores indicating the degree of order of dermis collagen fiber bundle before the skin conditioning-ameliorating agent was applied to the mouse photo-aging model as obtained in a) above in accordance with the evaluation method of the present invention, the degree of amelioration of skin conditions in the dexamethasone-applied group was 1.71/0.82=2.09, while it was 0.78/0.82=0.95 in the ethanol-applied group. Alternatively, taking the influence of ethanol that is a base for lotion into consideration, the degree of amelioration of skin conditions with the application of the dexamethasone was calculated by dividing the average scores of the dexamethasone-applied group by the average scores of the ethanol-applied group, resulting in 1.71/0.78=2.28.

In this way, from the fact that the degree of order of dermis collagen fiber bundle was remarkably improved after application of a dexamethasone lotion as compared with the degree before application, it can be judged that dexamethasone has an excellent wrinkle-ameliorating effect and a lotion containing it is useful as a composition for topical application to skin for amelioration of wrinkles according to the evaluation method of the present invention.

As described above, a wrinkle-ameliorating effect of the dexamethasone lotion was found from scanning electron microphotographs of the skin surface morphology. Similarly, the dexamethasone lotion was judged to be useful as a composition for topical application to skin for amelioration of wrinkles.

2) Evaluation of Chapped Skin-ameliorating Agents Using Guinea Pig Damaged Skin Model a) Preparation of Chapped Skin Model Three Hartley white guinea pigs (body weight 250–300 g) were shaven on the back and Vaseline containing 1% sodium laurylsulfate was subcutaneously administered to the shaven portions for 48 hours. Two days after completion of the administration, the guinea pigs served as the chapped skin models. The portions of the skin on the back of the three guinea pig chapped skin models were excised to prepare dermis specimens respectively. Their electron microphotographs were taken and the degree of order of the dermis collagen fiber bundle were scored and judged in the same manner as described above. As a result, an average of the score in the three guinea pig chapped skin models was 0.89.

b) Evaluation and Screening of Chapped Skin-ameliorating Agents

An ethanol solution containing 0.5% of polymethacryloyl-phosphatidylcholine was applied on the skins on the back of the three guinea pig chapped skin models as obtained by the same manner as described above everyday for 8 weeks, thereby increasing the score of the degree of order of the dermis collagen fiber bundle to 2.11 as an average of the score in the three guinea pig chapped skin models. According to the evaluation method of the present invention, comparing this value with the score as obtained in a) above, which indicates the degree of order of the dermis collagen fiber bundle before applying the above-described ethanol solution to the guinea pig chapped skin models, the degree of amelioration of skin conditions is calculated as 2.11/0.89=2.37. From the fact that the degree of order of the dermis collagen fiber bundle is remarkably increased after the application of the ethanol solution containing polymethacryloylphosphatidylcholine as compared with that before its application, polymethacryloylphosphatidylcholine is judged as an excellent chapped skin-ameliorating agent according to the evaluation method of the present invention.

Further, a difference of the skin surface morphologies of the guinea pig chapped skin models were observed by naked eyes before and after the application of the above ethanol solution containing polymethacryloylphosphatidylcholine and, as a result, chapped skins were recovered well after the application.

(2) Method of Producing the Composition for Topical Application to Skin According to the Present Invention The method of producing the composition for topical application to skin according to the present invention relates to the method of producing the composition for topical application to skin containing the skin conditioning-ameliorating agent and comprises steps of providing an animal having at least one skin portion with bad conditions, applying to the skin portion the composition for topical application to skin once per day for consecutive 8 weeks in an amount of 0.01 g/10 cm$^2$/one application, taking microphotographs of a dermis specimen prepared by excising at least a part of the skin portion, at a magnification of 100 to 10,000, preferably 500 to 2,500, judging the microphotographs based on the above-described criterion for judging to determine the degree of order of dermis collagen fiber bundle of the part of the skin portion before and after application of the composition, and adjusting the content of the skin conditioning-ameliorating agent so that the value calculated by dividing the degree of order of dermis collagen fiber bundle after application of the composition by that before application should be not less than 1.5.

[Criterion for judging]

0: No collagen fiber bundle structure is observed in all observation area.

1: Disintegration or conversion to abnormal structure of collagen fiber bundle structure is observed in more than half of the observation area.

2: Disintegration or denaturation of collagen fiber bundle structure is observed in part, but almost normal structure is retained as a whole.

3: Normal collagen fiber bundle structure is observed over the whole area with almost no disintegration and denaturation.

The method of producing the composition for topical application to skin according to the present invention can be carried out in the same manner as the method of producing the conventional compositions for topical application to skin, except that the method of the present invention comprises the step of adjusting the content of the skin conditioning-ameliorating agent as described above. For example, the method may comprise determining the composition of the composition for topical application to skin to be prepared corresponding to its dosage form with adjusting the content of the skin conditioning-ameliorating agent as described above, selecting an appropriate method among the methods usually applied to production of the composition for topical application to skin having the above-described dosage form, and producing it in accordance with the selected method.

The composition for topical application to skin obtained by such a production method according to the present invention shows an excellent effect for ameliorating abnormality of skin resulting in worsening of the skin conditions of the animal having at least one skin portion with bad conditions, which is used when the content of the above-described skin conditioning-ameliorating agent is adjusted or abnormality of skin similar thereto. For example, in the case of using the mouse photo-aging model as described in detail in (1) above as the animal having at least one skin portion with bad conditions, the composition for topical application to skin excellent in a wrinkle-ameliorating effect can be obtained since the above model is typical as the wrinkle model. In the case of the guinea pig chapped skin model, which is typical as the chapped skin model, the composition for topical application to skin excellent in a chapped skin-ameliorating effect can be obtained.

Further, the compositions for topical application to skin obtained by the production method of the present invention are exemplified by such as cosmetics or medicines for topical application to skin including anti-inflammatory agents, anti-fungal agents, and the like. Among these, cosmetics are preferred. Further, among the cosmetics, preferred are wrinkle-ameliorating cosmetics and chapped skin-ameliorating cosmetics, to which the animal model excellent in the above production method is applicable.

EXAMPLE

The present invention will be illustrated in further detail with the following Example.

A cosmetic in the form of cream was prepared according to the formulation shown in Table 1 below. Specifically, component B was kneaded, which was diluted by component A. Then, the mixture was heated to 80° C. and component C, which had been adjusted to have a temperature of 80° C. in advance, was gradually added to the mixture to give an emulsion. The emulsion was stirred and cooled to obtain a cream. The numerals in the formulation means part by weight.

Then, the resulting four kinds of cosmetics were applied to a skin portion to be tested of the mouse photo-aging models, which were prepared by exposing mice to the ultraviolet light irradiation for 10 weeks as described in the above mouse photo-aging model, once per day for consecutive 8 weeks in an amount of 0.01 g/10 cm$^2$/one application to examine changes of the degree of order of dermis collagen fiber bundle of the above skin portion before and after the application of the cosmetics. In this occasion, the degrees of order of dermis collagen fiber bundles were measured by taking microphotographs of dermis specimens, which have been prepared by excising parts of the above skin portions, at a magnification of 2,500 and judging the microphotographs thus obtained in accordance with the criterion for judging of 0 to 3 as described above. Evaluation was carried out using the value calculated by dividing the degree of order of the dermis collagen fiber bundle measured by the above method after the application by that before the application. The results are shown in Table 1 as the degree of ameliorating collagen fiber bundle.

Separately, forty panelists suffering from wrinkles were divided arbitrarily into four groups (No. 1 to 4) each containing ten people and were let have the cosmetics 1 to 4 as obtained above by the usual method for consecutive two months so that the cosmetics were each applied to the group to which the same number was designated. After the period of use, the degree of amelioration of wrinkles was examined by questionnairing. The results are also shown in Table 1.

From these results, it can be found that the evaluation results by the evaluation method of the present invention correlate well with the results obtained by the conventional method using panelists.

Further, the measurement results of the degree of amelioration of collagen fiber bundle can be applied to the production method of the present invention. Namely, when the composition for topical application to skin for ameliorating wrinkles is produced by adding dexamethasone to the cosmetic 1 in Table 1, it can be understood that dexamethasone can be added in an amount more than about the amount used in the cosmetic 3 shown in Table 1. Similarly, the amount used in the cosmetic 4 shown in Table 1 is enough for becromethasone, suggesting that it is possible to consider the smaller amount than that.

TABLE 1

|   |   | Amount added (part by weight) | | | |
|---|---|---|---|---|---|
|   | Component | Cosmetic 1 | Cosmetic 2 | Cosmetic 3 | Cosmetic 4 |
| A | microcrystal-line wax | 5 | 5 | 5 | 5 |
|   | liquid paraffin | 10 | 10 | 10 | 10 |
|   | simethicone | 10 | 10 | 10 | 10 |
|   | dexamethasone | — | 0.0001 | 0.0005 | 0.05 |
|   | becromethasone | — | — | — | — |
| B | triglycerol diisostearate | 5 | 5 | 5 | 5 |
|   | 70% maltitol solution | 10 | 10 | 10 | 10 |
|   | 1,3-butanediol | 5 | 5 | 5 | 5 |
|   | methylparaben | 0.3 | 0.3 | 0.3 | 0.3 |
| C | water | 54.7 | 54.7 | 54.7 | 54.7 |
| degree of amelioration of collagen fiber bundle | | 1.21 | 1.35 | 1.52 | 2.03 |
| amelioration of wrinkles (Number of people) | good | 0 | 2 | 4 | 6 |
|   | moderate | 10 | 8 | 6 | 4 |
|   | bad | 0 | 0 | 0 | 0 |

INDUSTRIAL APPLICABILITY

The present invention can provide a means of appropriately evaluating skin conditioning-ameliorating agents or compositions for topical application to skin containing the agent for ameliorating skin conditions such as wrinkles, chapped skin, and the like, or preventing such skin conditions from getting worse. The present invention can provide a method of producing a composition for topical application to skin containing a skin conditioning-ameliorating agent, wherein the composition for topical application to skin has a sufficient skin conditioning-ameliorating effect.

What is claimed is:

1. A method for evaluating a preparation for skin condition amelioration using an animal having at least one skin site in compromised condition having a degree of order of dermis collagen fiber bundles, which comprises the steps of:

applying the preparation to the skin site, and evaluating under a microscope a change in the degree of order of dermis collagen fiber bundles at the skin site before and after applying the preparation to the skin site.

2. The method as claimed in claim 1, wherein said bad conditions are wrinkles or chapped skin.

3. The method as claimed in claim 1, wherein said animal is a mouse having a skin site damaged by ultraviolet light irradiation or a guinea pig having a skin site on the back shaven and damaged by an anionic surfactant.

4. The method as claimed in claim 1, wherein said degree of order of dermis collagen fiber bundle is measured by taking microphotographs of a dermis specimen prepared by excising at least a part of the skin portion, at magnifications of 100 to 10,000 and judging the microphotographs based on the following criterion:

[Criterion for judging]

0: No collagen fiber bundle structure is observed in all observation area.

1: Disintegration or conversion to abnormal structure of collagen fiber bundle structure is observed in more than half of the observation area.

2: Disintegration or denaturation of collagen fiber bundle structure is observed in part, but almost normal structure is retained as a whole;

3: Normal collagen fiber bundle structure is observed over the whole area with almost no disintegration and denaturation.

5. A method for evaluating a preparation for skin condition amelioration, which comprises the steps of:

(a) providing an animal having at least one skin site in compromised condition having a degree of order of dermis collagen fiber bundles, (b) applying the preparation to the skin site, (c) taking microphotographs of a specimen of dermis prepared by excising at least a part of skin at the skin site, (d) judging the microphotographs based on the following scoring system to determine the degree of order of dermis collagen fiber bundle of the part of the skin before and after application of the preparation, wherein said scoring system comprises the following criteria:

(i) a score of 0 indicates that no collagen fiber bundle structure is observed in all observation area;

(ii) a score of 1 indicates that disintegration of conversion to abnormal structure of collagen fiber bundle structure is observed in more than half of the observation area;

(iii) a score of 2 indicates that disintegration or denaturation of collagen fiber bundle structure is observed in part, but almost normal structure is retained as a whole; and (iv) a score of 3 indicates that normal collagen fiber bundle structure is observed over the whole area with almost no disintegration and denaturation; and (e) changing formulation of the preparation and repeating steps (a) to (d) until a value calculated by dividing the degree of order of skin dermis collagen fiber bundle after application of the preparation by that before application is not less than 1.5.

6. The method as claimed in claim 5, wherein said composition for topical application to skin is a wrinkle-ameliorating cosmetic.

7. The method as claimed in claim 5, wherein said composition for topical application to skin is a chapped-skin ameliorating agent.

8. The method as claimed in claim 1, wherein, in the application step, the preparation is applied approximately once a day in an amount of 0.01 g/10 $cm^2$ at a time for eight consecutive weeks, and in the evaluation step, the change is evaluated at magnifications of 100 to 10,000.

9. A method of producing a preparation for skin condition amelioration, comprising the steps of:

(i) evaluating a candidate preparation according to claim 1; and (ii) selecting the preparation if the degree of order of dermis collagen fiber bundles is higher than a pre-selected value; and (iii) preparing a final preparation comprising the preparation if selected in step (ii).

10. A method for ameliorating skin conditions of a mammal, comprising producing a preparation according to claim 9 and applying the preparation onto a compromised skin site of the mammal until the skin conditions are ameliorated.

11. The method as claimed in claim 10, wherein the compromised conditions are wrinkles.

12. The method as claimed in claim 5, wherein, in step (b), the preparation is applied approximately once a day in an amount of 0.010.01 g/10 $cm^2$ at a time for eight consecutive weeks, and in step (c), the microphotographs are at a magnification of 100 to 10,000.

* * * * *

UNITED STATES PATENT AND TRADEMARK OFFICE
CERTIFICATE OF CORRECTION

PATENT NO. : 6,340,677 B1
DATED : January 22, 2002
INVENTOR(S) : Nishimori et al.

It is certified that error appears in the above-identified patent and that said Letters Patent is hereby corrected as shown below:

Column 13,
Line 15, "observation area." should be changed to -- observation area;--
Line 18, "half of the observation area.." should be changed to -- half of the observation area; --

Column 14,
Line 41, "an amount of 0.010.01 g/10cm$^2$" should be changed to -- an amount of 0.01 g/10cm$^2$ --

Signed and Sealed this

First Day of June, 2004

JON W. DUDAS
*Acting Director of the United States Patent and Trademark Office*

UNITED STATES PATENT AND TRADEMARK OFFICE
CERTIFICATE OF CORRECTION

PATENT NO. : 6,340,677 B1
DATED : January 22, 2002
INVENTOR(S) : Nishimori et al.

It is certified that error appears in the above-identified patent and that said Letters Patent is hereby corrected as shown below:

Column 13,
Line 42, "disintegration of conversion" should be changed to -- disintegration or conversion --

Column 14,
Line 14, "composition for topical application" should be changed to -- preparation for topical application --
Line 17, "composition for topical application" should be changed to -- preparation for topical application --

Signed and Sealed this

Fifth Day of October, 2004

JON W. DUDAS
*Director of the United States Patent and Trademark Office*

(12) EX PARTE REEXAMINATION CERTIFICATE (4856th)
United States Patent
Nishimori et al.

(10) Number: US 6,340,677 C1
(45) Certificate Issued: Sep. 30, 2003

(54) METHOD OF EVALUATION OF SKIN CONDITIONING-AMELIORATING AGENTS AND METHOD OF PRODUCING COMPOSITIONS FOR TOPICAL APPLICATION TO SKIN

(75) Inventors: Yasutomo Nishimori, Yokohama (JP); Katsuo Matsumoto, Yokohama (JP); Yukiko Kenjo, Yokohama (JP)

(73) Assignee: Pola Chemical Industries Inc., Shizuoka (JP)

Reexamination Request:
No. 90/006,337, Jul. 26, 2002

Reexamination Certificate for:
Patent No.: 6,340,677
Issued: Jan. 22, 2002
Appl. No.: 09/381,149
Filed: Sep. 13, 1999

(22) PCT Filed: Mar. 4, 1998
(86) PCT No.: PCT/JP98/00896
§ 371 (c)(1), (2), (4) Date: Sep. 13, 1999
(87) PCT Pub. No.: WO98/40045
PCT Pub. Date: Sep. 17, 1998

(30) Foreign Application Priority Data
Mar. 11, 1997 (JP) .............................. 9-074353

(51) Int. Cl.⁷ ..................... A61K 31/56; B05D 3/00
(52) U.S. Cl. ................. 514/169; 514/171; 514/557; 514/574; 427/2.11
(58) Field of Search ................. 514/169, 171, 514/557, 574; 427/2.11

(56) References Cited

U.S. PATENT DOCUMENTS 3,856,934 A 12/1974 Kigman
4,370,322 A 1/1983 Busse et al.

FOREIGN PATENT DOCUMENTS

CH 662 508 A5 10/1987

OTHER PUBLICATIONS

G. Bryce, et al., "Retinoid Effects on Photodamaged Skin," *Method in Enzymology*, vol. 190, pp. 352–360, 1990.

L. Kligman, et al., "Topical Retinoic Acid Enhances the Repair of Ultraviolet Damaged Dermal Connective Tissue," *Connective Tissue Research*, vol. 12, pp. 139–150, 1984.

L. Kligman, "Effects of All–Trans–Retinoic Acid on the Demis of Hairless Mice," *Journal of the American Academy of Dematology*, vol. 15, pp. 15, pp. 779–785, 1986.

L. Kligman, et al., "Sunscreens Promote Repair of Ultraviolet Radiation–Induced Dermal Damage," *Journal of Investigative Dermatology*, vol. 81, pp. 98–102, 1983.

L. Kligman, "Connective Tissue Photodamage in the Hairless Mouse is Partially Reversible," *Journal of Investigative Dermatology*, vol. 88, No. 3, pp. 12s–17s, March Supplement, 1987.

*Primary Examiner*—Theodore J. Criares

(57) ABSTRACT

An object of the present invention is to provide a means of appropriately evaluating a skin conditioning-ameliorating agent for ameliorating bad skin conditions or preventing the skin conditions from getting worse and a composition for topical application to skin containing the above agent. The invention provides a method for evaluating a skin conditioning-ameliorating agent or a composition for topical application to skin containing the same using an animal having at least one skin portion with bad conditions, which comprises applying to the skin portion the skin conditioning-ameliorating agent or the composition for topical application to skin containing the agent and evaluating the agent or the composition using as an index changes of the degree of order of dermis collagen fiber bundle at the skin portion before and after application.

EX PARTE REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–12 and is confirmed.

* * * * *